US00PP30808P2

(12) United States Plant Patent
Hansen

(10) Patent No.: US PP30,808 P2
(45) Date of Patent: Aug. 13, 2019

(54) ***SEDUM* PLANT NAMED 'BUNDLE OF JOY'**

(50) Latin Name: ***Sedum* hybrid**
Varietal Denomination: Bundle of Joy

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,523

(22) Filed: Nov. 28, 2018

(51) Int. Cl.
*A01H 5/00* (2018.01)
*A01H 6/32* (2018.01)

(52) U.S. Cl.
USPC ..... Plt./479
CPC ..... *A01H 6/32* (2018.05); *A01H 5/00* (2013.01)

(58) Field of Classification Search
USPC ..... Plt./479
CPC ..... A01H 5/00; A01H 5/02
See application file for complete search history.

*Primary Examiner* — Kent L Bell

(57) ABSTRACT

The new and distinct cultivar of perennial *Sedum* plant named 'Bundle of Joy' is characterized by drought-tolerant, winter-hardy, tight, compact mounds. The flowers are near-white on stems producing dense clusters that cover the plant in late summer. The new plant stays tightly compact and resists opening in the center later in the season. The new plant is useful for landscaping as a specimen plant or en masse.

1 Drawing Sheet

Botanical designation: *Sedum* hybrid.
Cultivar denomination: 'Bundle of Joy'.

STATEMENT REGARDING PRIOR DISCLOSURES UNDER 37 CFR 1.77(b)(6)

As of the filing date of this application no plants of *Sedum* 'Bundle of Joy' have been sold. On Dec. 1, 2017 the claimed plant was displayed with a photograph and brief description in a website operated by the Assignee, who obtained the plant and all information relating thereto, from the inventor. No plants of *Sedum* 'Bundle of Joy' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of *Sedum* or stonecrop plant, botanically known as *Sedum* and hereinafter referred to by the cultivar name 'Bundle of Joy'. There are over 300 recognized species of the genus *Sedum*.

The new plant is a whole plant mutation discovered by the inventor at a wholesale perennial nursery in Zeeland, Mich., USA in the Sep. 10, 2012 in a production field planting of *Sedum* 'Pure Joy' U.S. Plant Pat. No. 24,194.

The new *Sedum* plant was selected for its compact groundcover habit form together with the dense white flowering.

Asexual reproduction of *Sedum* 'Bundle of Joy' by vegetative cuttings at a wholesale perennial nursery in Zeeland, Mich., USA since the winter of 2015, has shown that the unique features of this new *Sedum* plant are stable and reproduced true to type in successive generations.

SUMMARY OF THE INVENTION

Plants of *Sedum* 'Bundle of Joy' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Bundle of Joy'. The following characteristics in combination distinguish 'Bundle of Joy' as a new and distinct *Sedum* plant unique from all other *Sedum* plants known to the inventor:

1. Short and compact plant habit.
2. Plants are drought tolerant and winter hardy to at least USDA zone 3.
3. Numerous, near-white flowers in dense clusters completely cover the plant in early August.
4. Stems and foliage stay tightly compact resistant to open in center of plant.

In comparison, 'Pure Joy' has pink bi-color flowers. Other similar varieties include: 'Eline' U.S. Plant Pat. No. 24,772 and 'Thundercloud'. 'Eline' has more upright habit, less dense flowering and the flowers are yellowish. 'Thundercloud' has taller and less dense habit.

BRIEF DESCRIPTION OF THE PHOTOGRAPH

The photograph of the new plant demonstrates the unique traits and the overall appearance of *Sedum* 'Bundle of Joy'. The colors are as accurate as reasonably possible with color reproductions of this type. Variations in ambient light spectrum, source and direction may cause the appearance of minor variation in color. The plants used in the photographs were five-year old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
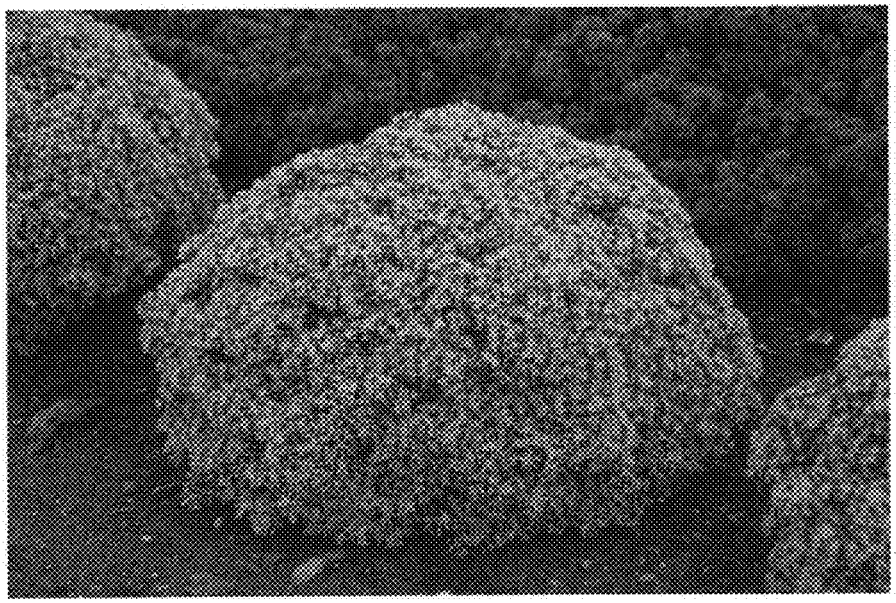
FIG. 1 shows the plant in full flower habit.
Figure 2:
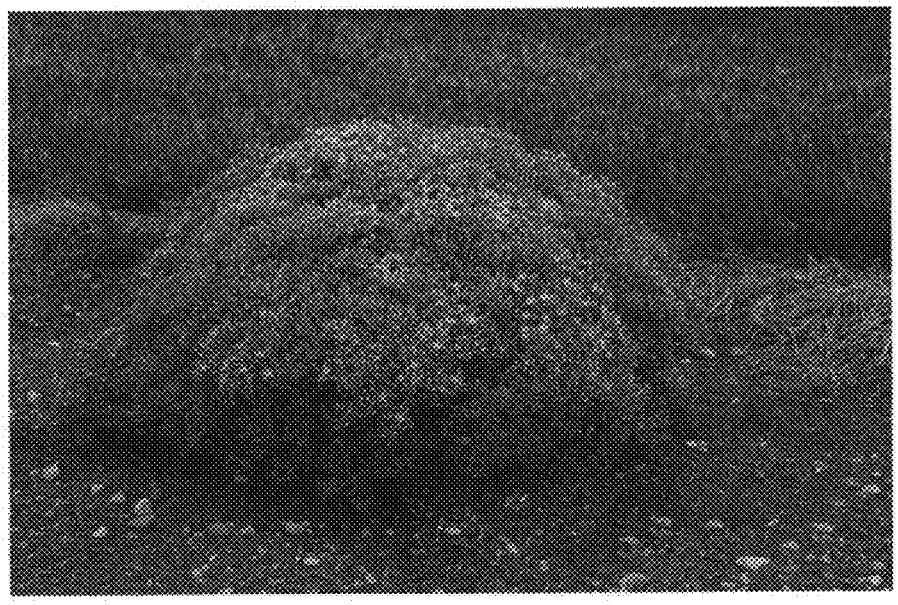
FIG. 2 shows the plant in early flowering with foliage, initial flowers and buds.

The following is a detailed description of five-year-old plants of the new cultivar as grown outdoors in a full sun trial plot and also as greenhouse grown specimens at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Bundle of Joy';

Parentage: Whole-plant mutation of *Sedum* 'Pure Joy';

Asexual propagation: Stem cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color.

Plant habit: Winter-hardy, succulent, herbaceous perennial; low mounded; multiple stiff stems, upright to outright, arising from a dense base; flower heads freely branching; dense and full, resists developing an open center later in the season;

Growth rate: Moderately vigorous;

Plant size: About 15.0 cm tall and 35.0 cm wide in full flower;

Main stems: Glabrous; about 16 per plant; diameter at stem base about 10.0 mm, average about 7.0 mm; about 18.0 cm long from base to initial flower cymes; maintaining foliage to base of stein; internodes average about 11.0 mm;

Main stem color: Nearest RHS 164B;

Lateral branches: Glaucous; to about 18.0 cm long and 6.0 mm diameter for lowest level branches, decreasing distally;

Lateral branch color: Blend between RHS 147C and RHS 146D;

Foliage: Opposite, simple; ovate; sessile; smooth; glaucous and glabrous abaxial and adaxial; abaxial and adaxial surface matte; base cuneate; apex rounded; margin dentate in distal one-half to one-third and entire in basal one-half to two thirds; thick, fleshy and succulent; to about 8.5 cm long, about 3.8 cm across near apex, and about 2.5 mm thick, average about 6.2 cm long, about 2.3 cm wide, about 2.0 mm thick, and base tapering to about 6.0 mm across; decreasing in size distally;

Foliage color: Developing leaves—adaxial surface nearest RHS N138A distally and nearest RHS 147C proximally, abaxial surface nearest RHS N138C distally and nearest RHS 147C distally; fully developed leaves at flowering time—adaxial surface nearest RHS 146B, abaxial surface nearest RHS 146B;

Venation: Pinnate; color same as surrounding leaf tissue on both surfaces;

Flower: Rotate; upright; perfect; actinomophic; in terminal compound cymes; freely flowering habit with up to 1000 per branched stem and 10,000 to 20,000 per plant, covering the entire foliage;

Flower size: About 15.0 to 17.0 mm across and 8.0 mm tall;

Flower facing: Upward to outwardly;

Flower fragrance: Not detected;

Flowering season: Beginning late summer and continuing for about four weeks in Zeeland, Mich.;

Longevity: Individual flower remain effective for about four to six days on the plant; individual flowers persistent;

Flower buds about one day prior to opening: Narrow conic; apex acute; base rounded; about 5.0 mm long and 2.0 mm across;

Flower bud color: Exposed petals longitudinal center nearest RHS 157A, petal apices faintly blushed with blend of RHS 64B, RHS 71B and RHS 187D, base nearest RHS NN155D;

Inflorescence: To about 20.0 cm tall from first branch and 32.0 cm across;

Petals: Typically five, rarely four; lanceolate; narrowly acute apex, base truncate, margin entire, glabrous; typically about 6.0 mm long and about 2.0 mm across;

Petal color: Adaxial base nearest RHS NN155C, distally faintly blushed with RHS 187D, abaxial center nearest RHS NN155A, basal margin nearest RHS NN155C apices faintly blushed with RHS 71B;

Calyx: Rotate; 3.0 mm across and 1.5 mm long;

Sepals: Typically five; lanceolate; entire; glabrous and nitid abaxial and adaxial; narrowly acute apex, truncate fused base; about 1.5 mm long and about 0.5 mm wide at fused base;

Sepal color: Nearest RHS 146B both adaxial and abaxial surfaces;

Peduncles: Glabrous; terete; strong and stiff, yet flexible; freely branching; angle erect in center to nearly 60 degrees from perpendicular for branched portions; about 20.0 cm long and 7.0 mm diameter;

Peduncle color: Blend between RHS 147C and RHS 146D;

Pedicels: Cylindrical; glabrous; glaucous to lustrous; strong and stiff, yet flexible; to about 8.0 mm long and 0.7 mm diameter;

Pedicel color: Nearest RHS 146D;

Androecium:

*Stamens*.—Typically five, rarely up to ten; to 7.0 mm long.

*Filaments*.—Thin; terete; upright; fused to petal base; about 6.5 mm long and about 0.5 mm diameter; color nearest RHS 155D proximally, nearest N155B distally.

*Anthers*.—Ellipsoidal; basifixed; about 0.5 mm long and about 0.3 mm wide; color nearest RHS 185A on initial anthesis, nearest RHS N187A at end of flowering.

*Pollen*.—Not observed; sterile.

Gynoecium: Typically five, rarely four; cylindrical, conic in distal one third; to 6.0 mm long;

*Style*.—About 5.0 mm long and 1.5 mm diameter near middle; glabrous; color nearest RHS 149D, blushed distally nearest RHS 187D.

*Stigma*.—Minute; color nearest 187D.

*Ovary*.—Nearly cylindrical, tapering at apex to style; about 5.5 mm long and 1.5 mm diameter at base;

color nearest RHS NN155C with slightly midrib blush of nearest RHS 61A.

Seed and fruit: Sterile;

Disease and pest resistance: Plants of the new *Sedum* 'Bundle of Joy' grow best with good drainage, full sun and moderate to low fertility. 'Bundle of Joy' is cold hardy from USDA zones 3 to 9. 'Bundle of Joy' tolerates heavy rains and wind and does not tend to develop an open center later in the season as many other stonecrop cultivars do. Other pest and disease resistance and tolerance outside that normal for stonecrop is not known.

It is claimed:

1. A new and distinct perennial *Sedum* plant named 'Bundle of Joy' as herein described and illustrated.

* * * * *